United States Patent
Bengtsson et al.

(10) Patent No.: US 11,007,327 B2
(45) Date of Patent: May 18, 2021

(54) PRE-FILLED DISPOSABLE INJECTION DEVICE

(71) Applicant: Novo Nordisk A/S, Bagsvaerd (DK)

(72) Inventors: Henrik Bengtsson, Taastrup (DK); Mads Schenstroem Stefansen, Copenhagen OE (DK); Lars Eilertsen, Fredensborg (DK); Henning Graaskov, Bagsvaerd (DK); Claus Moser, Soeborg (DK); Thomas Bjarnsholt, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 94 days.

(21) Appl. No.: 14/437,389

(22) PCT Filed: Oct. 22, 2013

(86) PCT No.: PCT/EP2013/072064
§ 371 (c)(1),
(2) Date: Apr. 21, 2015

(87) PCT Pub. No.: WO2014/064100
PCT Pub. Date: May 1, 2014

(65) Prior Publication Data
US 2015/0273161 A1      Oct. 1, 2015

Related U.S. Application Data

(60) Provisional application No. 61/720,623, filed on Oct. 31, 2012.

(30) Foreign Application Priority Data

Oct. 25, 2012 (EP) .................................. 12189993

(51) Int. Cl.
*A61M 5/32* (2006.01)
*A61M 5/315* (2006.01)
(Continued)

(52) U.S. Cl.
CPC .......... *A61M 5/3257* (2013.01); *A61M 5/001* (2013.01); *A61M 5/326* (2013.01);
(Continued)

(58) Field of Classification Search
CPC .. A61M 5/001; A61M 5/3202; A61M 5/3205; A61M 2005/3254
See application file for complete search history.

(56) References Cited

U.S. PATENT DOCUMENTS 3,134,380 A  *  5/1964  Armao .................. A61M 5/001
                                                                     604/198
3,354,881 A      11/1967  Bloch
(Continued)

FOREIGN PATENT DOCUMENTS

EP          0175583 A2     3/1986
EP          2246085 A1    11/2010
(Continued)

*Primary Examiner* — Quynh-Nhu H. Vu
(74) *Attorney, Agent, or Firm* — Wesley Nicolas

(57) ABSTRACT

The present invention relates to a pre-filled disposable injection device and a needle cannula in combination. The prefilled disposable injection device (1) is made from a housing (2) containing a non-exchangeable cartridge (10) for storing a liquid drug sufficient for a number of injections. The proximal end of the pre-filled injection device (1) carries the dose setting button (3) and the distal end carries the needle cannula (20) having a lumen (21) through which the settable dose is expelled. The distal end (23) of the needle cannula (20) is covered by a telescopic needle covering shield (30) which shield (30) can operate between a first position covering the tip (24) of the needle cannula (20) and a second retracted position allowing an injection to be performed. The shield (30) carries a cleaner (50) which cleans at least the tip (24) of the needle cannula (20) between successive injections such that the prefilled injection device (Continued)

can be used without changing the needle cannula (20) during its life cycle.

4 Claims, 9 Drawing Sheets

(51) Int. Cl.
*A61M 5/00* (2006.01)
*A61M 5/31* (2006.01)
*A61M 5/46* (2006.01)
*A61M 5/28* (2006.01)

(52) U.S. Cl.
CPC ........... *A61M 5/3286* (2013.01); *A61M 5/002* (2013.01); *A61M 5/288* (2013.01); *A61M 5/31548* (2013.01); *A61M 5/3202* (2013.01); *A61M 5/46* (2013.01); *A61M 2005/3118* (2013.01); *A61M 2005/3128* (2013.01); *A61M 2005/3247* (2013.01); *A61M 2005/3267* (2013.01); *A61M 2209/10* (2013.01); *F04C 2270/041* (2013.01)

(56) References Cited

U.S. PATENT DOCUMENTS

| | | | |
|---|---|---|---|
| 4,227,528 A | 10/1980 | Wardlaw | |
| 4,416,663 A * | 11/1983 | Hall | A61M 5/326 |
| | | | 604/198 |
| 4,507,118 A | 3/1985 | Dent | |
| 4,666,436 A | 5/1987 | McDonald et al. | |
| 5,342,320 A * | 8/1994 | Cameron | A61M 5/3257 |
| | | | 604/192 |
| 5,378,233 A | 1/1995 | Haber et al. | |
| 5,505,694 A | 4/1996 | Hubbard et al. | |
| 6,099,504 A | 8/2000 | Gross et al. | |
| 6,159,184 A | 12/2000 | Perez et al. | |
| 6,203,529 B1 * | 3/2001 | Gabriel | A61M 5/3202 |
| | | | 604/192 |
| 6,447,480 B1 | 9/2002 | Brunel | |
| 6,547,764 B2 * | 4/2003 | Larsen | A61M 5/326 |
| | | | 604/110 |
| 6,796,967 B2 | 9/2004 | Jensen | |
| 7,458,962 B2 | 12/2008 | McWethy et al. | |
| 7,462,168 B2 * | 12/2008 | Stonehouse | A61M 5/326 |
| | | | 604/192 |
| 7,641,637 B2 | 1/2010 | Gerondale et al. | |
| 7,988,675 B2 | 8/2011 | Gillespie, III et al. | |
| 8,647,306 B2 | 2/2014 | Schwirtz et al. | |
| 8,663,174 B2 * | 3/2014 | Zaiken | A61M 5/326 |
| | | | 604/198 |
| 2005/0015055 A1 | 1/2005 | Yang | |
| 2005/0215952 A1 | 9/2005 | Brunel et al. | |
| 2008/0188813 A1 * | 8/2008 | Miller | A61M 5/14566 |
| | | | 604/189 |
| 2009/0124971 A1 | 5/2009 | Shue et al. | |
| 2010/0234811 A1 * | 9/2010 | Schubert | A61M 5/326 |
| | | | 604/198 |
| 2011/0021988 A1 * | 1/2011 | Jensen | A61M 5/3245 |
| | | | 604/110 |
| 2011/0118667 A1 * | 5/2011 | Zaiken | A61M 5/326 |
| | | | 604/138 |
| 2011/0257603 A1 * | 10/2011 | Ruan | A61M 5/326 |
| | | | 604/198 |
| 2012/0029469 A1 * | 2/2012 | Horvath | A61M 5/32 |
| | | | 604/506 |
| 2012/0041368 A1 * | 2/2012 | Karlsson | A61M 5/326 |
| | | | 604/111 |
| 2012/0059333 A1 | 3/2012 | Singhal | |
| 2012/0150125 A1 * | 6/2012 | Karlsson | A61M 5/326 |
| | | | 604/198 |
| 2012/0289906 A1 * | 11/2012 | Jones | A61M 5/24 |
| | | | 604/207 |
| 2013/0204186 A1 * | 8/2013 | Moore | A61M 5/326 |
| | | | 604/111 |
| 2013/0245561 A1 * | 9/2013 | Kouyoumjian | A61M 5/3294 |
| | | | 604/191 |
| 2014/0243755 A1 * | 8/2014 | Slemmen | A61M 5/3257 |
| | | | 604/198 |

FOREIGN PATENT DOCUMENTS

| | | |
|---|---|---|
| JP | S4923675 A | 3/1974 |
| JP | 2005516646 A | 6/2005 |
| WO | 9007349 A1 | 7/1990 |
| WO | 03061735 A1 | 7/2003 |
| WO | 2008/077706 A1 | 7/2008 |
| WO | 2009040605 A1 | 4/2009 |
| WO | 2009152542 | 12/2009 |
| WO | 2010079016 A1 | 7/2010 |
| WO | 2010090747 A1 | 8/2010 |
| WO | 2011095483 A1 | 8/2011 |
| WO | 2011095489 A1 | 8/2011 |
| WO | 2012003516 | 1/2012 |
| WO | 2012072552 A1 | 6/2012 |

* cited by examiner

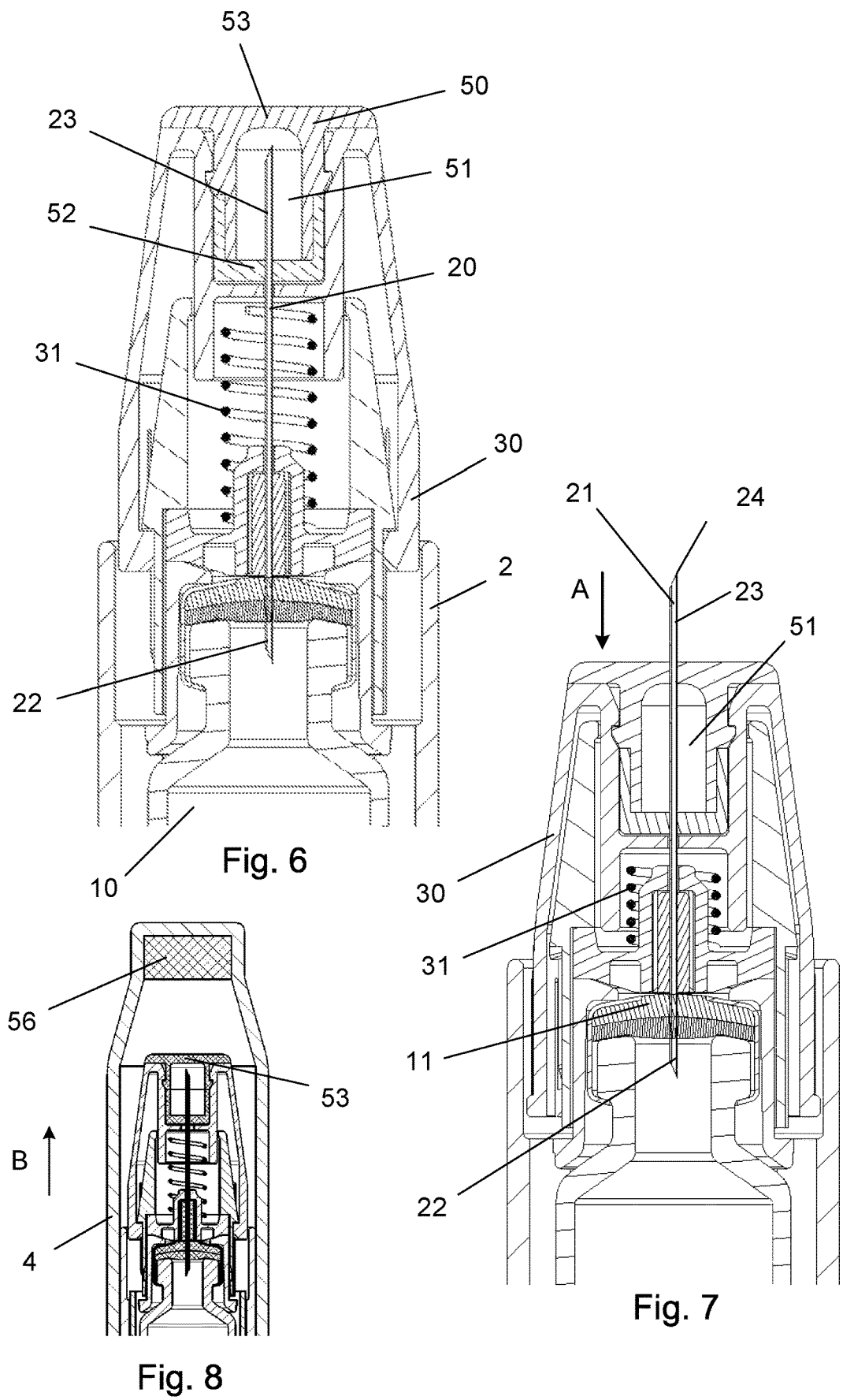

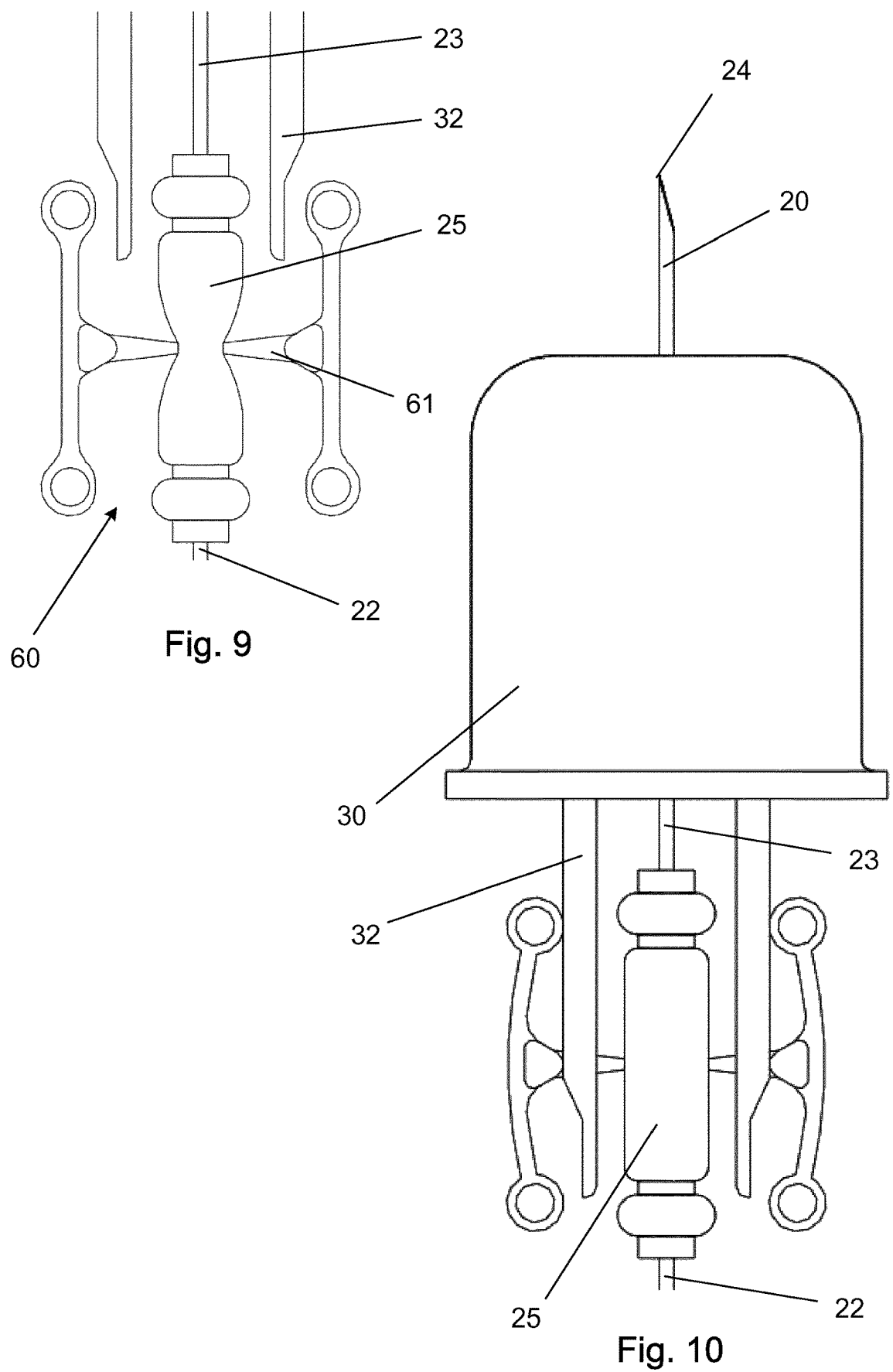

PRE-FILLED DISPOSABLE INJECTION DEVICE

CROSS-REFERENCE TO RELATED APPLICATIONS

This application is a 35 U.S.C. § 371 National Stage application of International Application PCT/EP2013/072064 (published as WO 2014/064100), filed Oct. 22, 2013, which claims priority to European Patent Application 12189993.4, filed Oct. 25, 2012; this application claims priority under 35 U.S.C. § 119 to U.S. Provisional Application 61/720,623; filed Oct. 31, 2012.

THE TECHNICAL FIELD OF THE INVENTION

The invention relates to prefilled disposable injection devices which are discarded when emptied. The invention especially relates to such pre-filled injection device having a needle cannula which is shielded and which shield carries a cleaner for cleaning at least the tip of the attached needle cannula between injections.

Further the invention relates to a method of performing an injection especially during self-treatment of a person with diabetes.

DESCRIPTION OF RELATED ART

U.S. Pat. No. 7,641,637 disclose an injection device with an injection needle which injection device is precharged with an amount of botulinum toxin and utilized for a multiple number of injections.

A problem with such injection devices is that the needle is unprotected between injections and therefore liable to be damaged. Further, bacteria can grow on the needle cannula and result in infections.

Pen needles for multiple uses are described in WO 2010/090747 and in US 2012/0059333. These pen needles are stored between injections in a needle container having a compartment containing a cleaning solvent cleaning the injection part of the needle cannula.

However, should the user for some reason not re-cap the injection part of the needle cannula with the container between injections, the tip will not be cleaned between injections. Also, these pen needles are unprotected following an injection and even more vulnerable as the user has to re position the container after each injection.

Pen needles having a shield for covering the front-part of the needle cannula are disclosed in WO 2008/077706 and in WO2010/079016.

Such pen needles are usually delivered to the user individually packed in a sterilized container such that one single container holds one sterilized pen needle. Once the container is opened, the pen needle is no longer sterile.

It is further known to have an exchangeable needle shielding unit with a telescopic shield carrying a chamber containing a cleaning solvent. In this way the tip of the needle cannula is stored inside the chamber containing the cleaning solvent between successive injections. During injections the tip of the needle cannula penetrates through a membrane provided in the distal chamber wall and thus moves out of the chamber containing the cleaning solvent. Such an exchangeable needle shielding device is e.g. disclosed in U.S. Pat. Nos. 4,416,663 and 4,666,436.

Since this needle shielding device can be moved from one syringe to another, the user must before each single injection make sure that an adequate amount of cleaning solvent is present in the chamber. Once the chamber is empty, the tip of the needle cannula is no longer cleaned between injections.

As the prior art illustrates handling of the injection needle between injections is a major problem for users of injection devices for self-treatment. A great number of risks are involved:
 Risk of needle stick injuries,
 Risk of damaging the needle tip,
 Risk of forgetting extra injection needles for replacement,
 In order to avoid these risks, users sometime decide to reuse the same injection needle for multiple injections; however, this also involves a number of risks, e.g.:
 Risk of needle stick injuries,
 Risk of skin infections,
 Risk of needle clogging.

DESCRIPTION OF THE INVENTION

It is an object of the present invention to eliminate or at least dramatically reduce these risks thus enabling a safer handling of the pre-filled injection device.

It is a particular object to provide a pre-filled injection device in which physical needle handling is heavily reduced and preferably totally eliminated.

The invention is defined in the attached claim 1 followed by a number of embodiments. The individual claims are explained in details in the following.

Accordingly, in one aspect of the present invention, the pre-filled disposable injection device and needle cannula in combination comprises:
 A housing containing a non-exchangeable drug-cartridge for storing a liquid drug sufficient for a number of injections,
 A settable dose setting mechanism having a dose setting button whereby a user can set or select a random size of a dose to be injected,
 A needle cannula having a lumen usable for the passage of the full content of drug in the non-exchangeable drug-cartridge through an initial injection followed by a successive number of subsequent injections, the needle cannula has a front-part carrying the tip and a back-part for entering the cartridge,
 A telescopic needle covering shield, which shield distally carries a cleaner and is operational between a first position and a second position;
  The first position defined as a position in which the telescopic shield is in an extended position covering a tip of a front-part of the needle cannula,
  The second position defined as a position in which the telescopic shield is retracted such that at least the tip of the front-part of the needle cannula is exposed to perform an injection.

The lumen of the needle cannula is preserved in a sterile condition prior to the initial injection and resilient means are provided for automatically returning the shield to its first position following both the initial injection and any of the subsequent injections. Further, the tip of the needle cannula is maintained inside the cleaner between injections.

Since the injection device together with the needle cannula is delivered ready to use in a sterile condition, the initial injection is always performed with a sterile needle cannula or at least through a sterile lumen. Hereafter the needle cannula is maintained attached to the injection device and cleaned between the subsequent injections. The fact that the needle cannula and the injection device is delivered in a ready-to-use state, and that the needle cannula is maintained attached to the injection device between injections substantially lowers the above risks as no needle handling is needed. At the same time at least the tip of the needle cannula is automatically protected by the shield from the instant the user pulls the device from the skin and until next injection. Further the tip of the needle cannula is cleaned between any of the successive injections thereby hindering or at least diminishing bacteria from forming at the tip of the needle cannula.

In one aspect of the invention, the needle cannula is permanently mounted to the housing and cannot be removed from the injection device such that the user is forced to use the same needle cannula to inject the entire content of the cartridge.

The overall concept of the invention is that the pre-filled injection device is delivered to the user with the needle cannula secured to the injection device either permanently or pre-mounted and with the lumen of the needle cannula in a sterile condition and usable for a continuous series of successive injections. The same needle cannula is thus dedicated to be used for several injections, preferably but not necessarily, to the number of injections available in the pre-filled injection device.

In the embodiment wherein the needle cannula is permanently mounted to the housing the entire injection device together with the needle cannula is discarded once the content of the cartridge has been injected, thereby once and for all avoiding any needle handling. The needle cannula is e.g. glued or welded to the housing or alternatively moulded to the housing. However the needle cannula could in this embodiment also be permanently secured to a hub which is then permanently clicked on to the housing. The decisive feature in this embodiment is that the needle cannula is non-removable such that it follows the life cycle of the pre-filled injection device i.e. a life-time needle cannula which follows the destiny of the pre-filled injection device.

As an example, the prefilled injection device can be prefilled with 3.0 ml of a liquid insulin. Once the content of insulin has been injected through a number of successive injections, the injection device with the permanently attached needle cannula is discarded. A draw-back is however should the needle cannula be damaged before the full amount of the insulin contained in the cartridge has been used, the remaining quantum of insulin most be discarded together with the pre-filled injection and the permanently attached needle cannula.

As the same needle cannula is used throughout the entire life-time of the injection device no needle handling is necessary. Thus the needle cannula is dedicated, and constructed, to the same life-time as the pre-filled injection device.

In another embodiment, the needle cannula is mounted in a hub to form a well-known needle assembly e.g. a pen needle, which is pre-mounted onto the injection device by the manufacturer. The hub could e.g. be provided with connecting means for connecting the needle assembly to the injection device in a traditional manner e.g. by using a thread or a bayonet coupling. The pre-filled injection device with the injection needle assembly pre-mounted is thus delivered to the user in a ready-to-use state and the needle cannula is also here dedicated and constructed to the same life time as the pre-filled device. However, should the needle cannula be damaged during use, the user has the option to exchange the needle assembly without the need of the manufacture. The user is therefore able to use the entire content of the liquid drug in the cartridge even should the needle cannula be damaged simply by replacing the pre-mounted needle assembly.

For both embodiments, the prefilled injection device and the attached needle cannula are delivered to the user in a sterile condition, or at least with a sterile lumen. Meaning that either the entire injection device with the needle cannula is packed in a sterile package, or at least the front part of the needle cannula is packed sterile.

After the sterility barrier has been broken and the initial injection performed, the tip of the needle cannula is maintained in the cleaner between the subsequent injections.

The cleaner can in one embodiment be a hollow chamber which contains a cleaning solvent. The cleaning solvent could also be confined in a sponge located in the hollow chamber. The cleaning solvent contained in the hollow chamber of the cleaner could be any conventional type of suitable sterilizing or disinfectant solution such as e.g. ethyl alcohol or the like.

Alternatively the cleaner can be a solid element which physically sweeps the outer surface of the needle cannula between injections. Such solid plug could be made from a polymer composition containing an anti-bacterial material.

In the hollow chamber solution, the chamber is preferably sealed distally and proximally by a self-sealing septum made from a suitable polymer. This polymer could also contain an anti-bacterial material. Further the fact that both septums are self-sealing means that the outer surface of the needle cannula slides against each septum at the penetration point, such that at least the distal septum physically sweeps the outer surface of the front part of the needle cannula.

When the needle cannula is maintained attached to the injection device between injections, there is a risk of clogging of the lumen. However, when the tip of the needle cannula is maintained submerged in a cleaning solvent between injections clogging is prevented. Further, a large variety of other means can be provided to prevent clogging of the lumen of the needle cannula.

In one embodiment the means for preventing clogging can be to prevent flow passage through the lumen of the needle cannula. If no drug is present in the lumen of the needle cannula, no clogging is possible. This prevention of passage can be made by any kind of valve, hereunder disconnecting the needle cannula from the drug cartridge or simply just corking the needle cannula with a plug. Such plug is preferably but not necessarily carried by the shield as in a previous embodiment.

In one embodiment, the needle cannula follows the axial movement of the telescopic needle shield, such that when the shield is in its first extended position the back part of the needle cannula is disconnected from the cartridge whereas when the shield is moved into its second position, the needle cannula follows this movement such that the back-part of the needle cannula connects to the cartridge. Following the injection when the shield is re-positioned into its first position, the back-part of the needle cannula decouples from the cartridge thereby hindering clogging.

The needle cannula is preferably mounted to an axially movable hub which is preferably forced forward by a hub spring inserted between the housing and the moveable hub. During injection, this axially movable hub moves proximally to connect the back part of the needle cannula with the interior of the cartridge. Once the pre-filled injection device and needle cannula is removed from the skin of the user following injection, the hub spring automatically moves the movable hub distally to disconnect the back part of the needle cannula from the cartridge.

In a further embodiment, the needle cannula and the movable hub locks the first time the shield is moved to its second position such that the back part of the needle cannula remains inserted into the cartridge for the successive injections.

Prior to the initial injection when the back part of the needle cannula is disconnected from the interior of the cartridge, this back part can be sterile confined in a rubber- or latex bag which is sealed to the movable hub and which bag is penetrated by the back part of the needle cannula once it enters into the cartridge.

When the telescopic needle shield is in its first extended position covering the front-part of the needle cannula, the shield is preferably locked by a locking mechanism. This locking mechanism prevents the shield from moving into its second retracted position. The locking is preferably done by a locking element which prevents the proximal movement of the needle shield and which locking element either by rotation or axial movement can be moved to a new position in which it allows the telescopic needle shield to be retracted.

Further a mechanism can be provided which provides the user the possibility of setting the length the needle shield can be retracted relatively to the prefilled injection device. This makes it possible for the user to select the length the front-part of the needle cannula penetrates into the body of the user.

The invention further relates to a method of injecting a plurality of settable doses of a liquid drug through a single needle cannula shielded by a spring-loaded shield and attached to a pre-filled injection device containing a pre-determined quantum of liquid drug.

The combined pre-filled injection device and shielded needle cannula is provided with resilient means, such as a spring, for repositioning of the shield and means for automatically cleaning at least of the tip of the shielded needle cannula between successive injections.

The cleaner is carried by the shield and as such axially movable in relation to the tip of the needle cannula.

The method comprising the steps of:
  (i) Taking the combined pre-filled injection device and needle cannula into use,
  (ii) Pushing a distal end of the combined pre-filled injection device and shielded needle cannula against the skin of a user thereby retracting the spring-loaded shield and inserting the tip of the shielded needle cannula into the skin of the user,
  (iii) Releasing one of the plurality of settable doses,
  (iv) Remove the distal end of the combined pre-filled injection device and shielded needle cannula from the skin thereby repositioning the shield to cover the tip of the needle cannula,
  (v) cleaning at least the tip of the shielded needle cannula using the cleaner before any subsequent injection,
  (vi) Perform the steps (ii) to (v) repeatedly over time until the pre-determined quantum of liquid drug is used, and
  (vii) Dispose of the combined prefilled injection device (1) and shielded needle cannula.

In a different embodiment, the invention relates to a method for self-treatment of a person with diabetes using a pre-filled injection device having a needle cannula mounted thereon.

The combined pre-filled injection device and needle cannula comprises:
  A housing containing a non-exchangeable cartridge for storing a liquid blood glucose regulating drug sufficient for a number of injections,
  A settable dose setting mechanism having a dose setting button whereby a user can set or select a random size of a dose to be injected,
  The needle cannula comprising a front part having a tip for penetrating the skin of the user, a back part for penetrating into the cartridge, and a lumen usable for the passage of the drug in the non-exchangeable cartridge through an initial injection followed by a successive number of subsequent injections,
  a telescopic needle covering shield distally carrying a cleaner, and which shield can operate between a first position and a second position;
    The first position being a position in which the telescopic shield is in an extended position covering the tip of the front part of the needle cannula,
    The second position being a position in which the shield is retracted such that at least the tip of the front part of the needle cannula is exposed to perform an injection, and
wherein at least the lumen of the needle cannula is preserved in a sterile condition prior to the initial injection and wherein resilient means are provided for automatically returning the shield to its first position following both the initial injection and any of the subsequent injections, and in which first position at least the tip of the front part of the needle cannula is contained within the cleaner between successive injections, the method comprising the steps of:
  (i) Taking the pre-filled injection device into use, preferably by removing at least the lumen of the needle cannula from its sterile confinement,
  (ii) Pushing a distal end of the pre-filled injection device against the skin of a user by which the telescopic needle shield moves from the first position to the second position,
  (iii) Releasing the set dose,
  (iv) Removing the distal end of the pre-filled injection device from the skin of the user such that the telescopic needle shield move axially from the second position to the first position, thereby repositioning the tip of the needle cannula inside the cleaner,
  (v) maintaining at least the tip of the shielded needle cannula inside the cleaner (50) until the next subsequent injection,
  (vi) Perform the steps (ii) to (v) successively over time until the liquid blood glucose regulating drug stored in the cartridge is substantially used, and
  (vii) Discard the combined prefilled injection device and shielded needle cannula.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle units specially designed for pen injections systems are defined in ISO standard No. 11608, part 2, and are often referred to as "pen needles". Pen needles have a front-end for penetrating into the user and a back-end for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 6-8 show a cross sectional view of the distal end of the pre-filled injection device.

FIG. 9-10 show a valve mechanism.

The figures are schematic and simplified for clarity, and they just show details, which are essential to the understanding of the invention, while other details are left out. Throughout, the same reference numerals are used for identical or corresponding parts.

Detailed Description of Embodiment

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

Figure 1A:
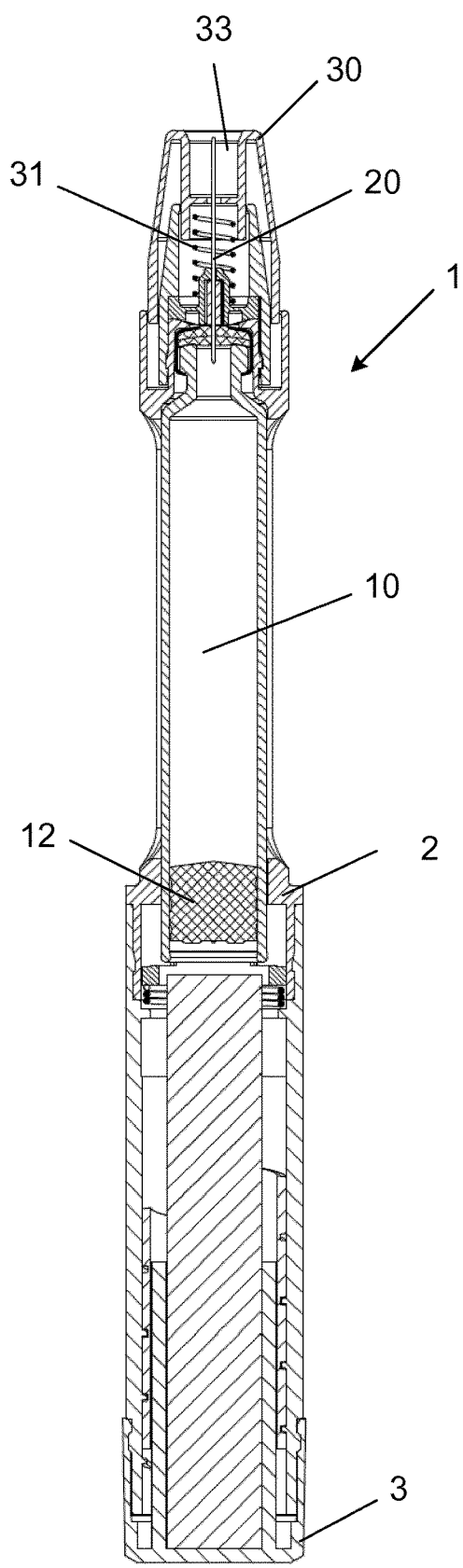
FIG. 1a-b show a cross sectional view of the pre-filled injection device.
Figure 1B:
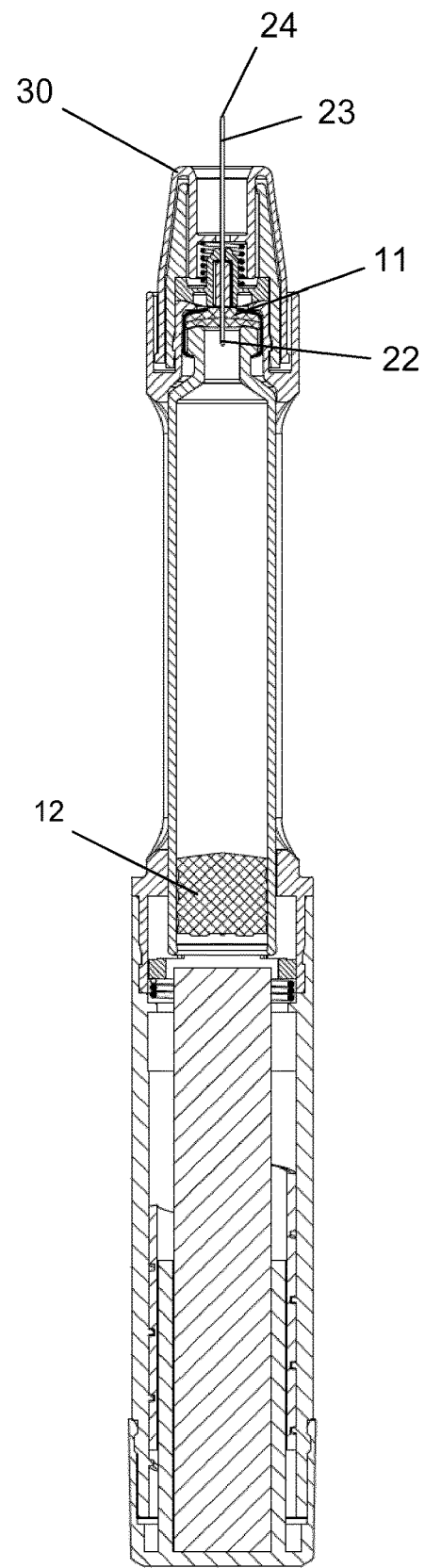

In that context it may be convenient to define that the term "distal end" in the appended figures is meant to refer to the end of the injection device which usually carries the needle cannula whereas the term "proximal end" is meant to refer to the opposite end pointing away from the injection needle and carrying the injection button 3 as depicted in FIG. 1a-b.

FIG. 1a-b discloses a pre-filled injection device 1 wherein a cartridge 10 is permanently embedded in the housing 2. At the proximal end a dose setting button 3 for setting a random dose size is provided. The distal end carries a needle cannula 20 which in the disclosed embodiment is permanently secured to the housing 3. The distal end of the housing 2 together with the needle cannula 20 and the needle shield 30 is preferably covered by a cap 4, an example of which is depicted in FIG. 8.

The needle cannula 20 has a proximal end 22 which penetrates through the septum 11 of the cartridge 10. Whenever the plunger 12 is moved in the distal direction inside the cartridge 10, an amount of the liquid drug contained in the cartridge 10 is pressed through the lumen 21 (See e.g. FIG. 6-7) of the needle cannula 20 thereby to be ejected from the distal end 23 of the needle cannula 20.

The distal end 23 of the needle cannula 20 and its pointed tip 24 is physically protected by a telescopic movable needle shield 30. This shield 30 is urged in the distal direction by a spring 31 encompassed between the housing 2 and the shield 30. The spring 31 could alternatively be moulded as a part of the housing 2 or as a part of the shield 30.

The shield 30 is provided with a holding portion 33 in which a cleaner 50 can be mounted. The cleaner 50 can, as explained later, be any kind of cleaner 50 suitable of cleaning the pointed tip 24 of the needle cannula 20 before performing an injection.

By rotating the dose setting button 3 a user can set a random dose size to be ejected from the injection device 1 as it commonly known. The mechanism ejecting the set dose can be any known mechanism, either manual or automatic. Once the user presses the distal end of the injection device 1 against the skin, the shield 30 is telescopically moved in the proximal direction against the bias of the spring 31 (indicated by the arrow "A" in FIG. 7)

The pre-filled injection device 1 with the cleaner 50 mounted in the holding portion 33 and its needle cannula 20 is delivered to the user ready-to-use in a sterile confinement.

Figure 2:
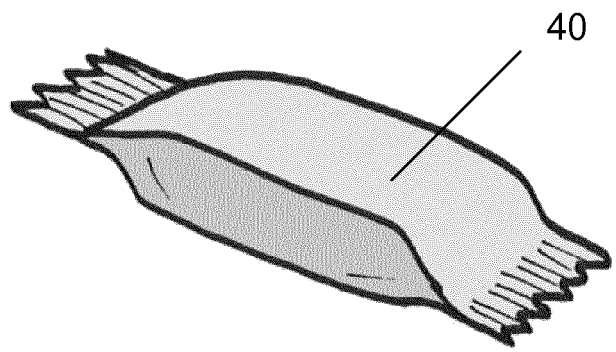
FIG. 2-3 show different examples of sterile packages.

FIG. 2 discloses an embodiment in which the injection device 1 with the needle cannula 20 is delivered packed in a sterile bag 40.

Figure 3:
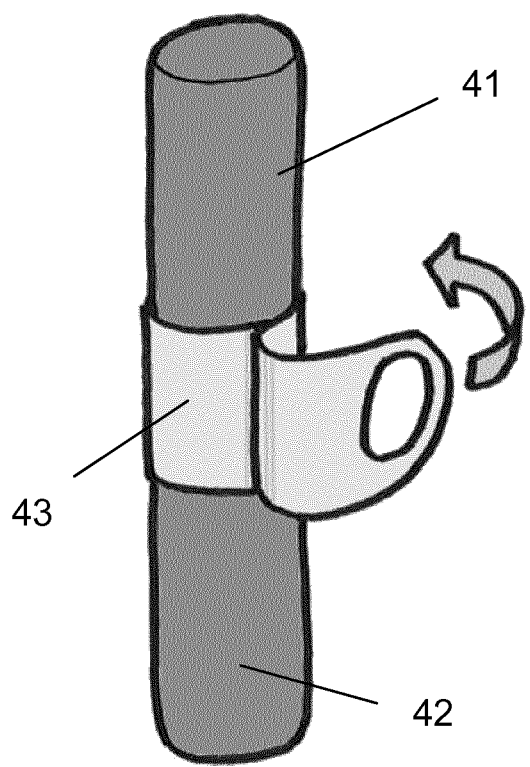

FIG. 3 discloses an embodiment in which the injection device 1 with the needle cannula 20 is delivered packed in a sterile two-part container 41, 42 secured together by a peelable ribbon 43.

Figure 4:
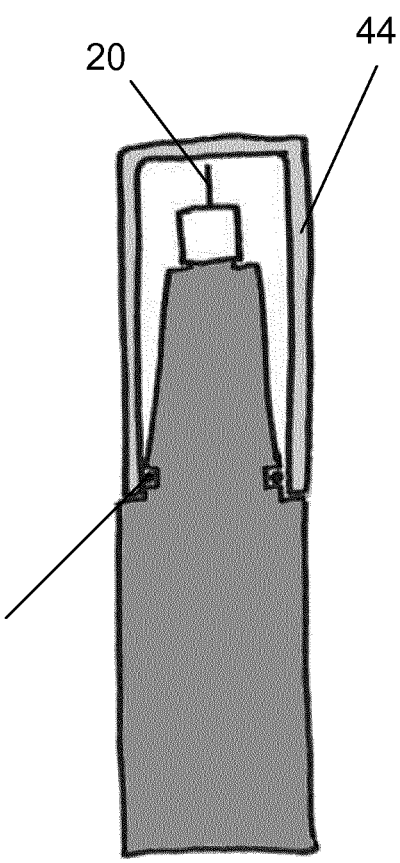
FIG. 4-5 show different examples of sterile caps or covers.

FIG. 4 discloses an embodiment in which the needle cannula 20 is covered by a cap 44 which is connected to the injection device 1 via a sealing 45 such that the interior of the cap 44 can be kept sterile.

Figure 5:
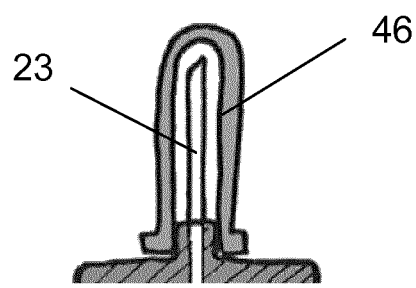

FIG. 5 discloses an embodiment in which the distal end 23 of the needle cannula 20 is covered by an inner cap 46 which is sealed to the injection device 1 to maintain the interior of the inner cap 46 sterile.

When the user starts using the pre-filled injection device he or she breaks the sterile barrier i.e. when the first initial injection is performed the lumen of the needle cannula 20 will be sterile.

FIG. 6 and FIG. 7 discloses an embodiment in which the telescopic movable needle shield 30 carries the cleaner 50 which has a chamber 51 holding a suitable amount of a liquid cleaning solvent. The proximal part 52 of the cleaner 50 and the distal part 53 of the cleaner 50 are formed from a material which the needle cannula 20 can easily penetrate. The two parts 52, 53 can be separate parts 52, 53 connected together in any known manner. The material used is preferably a rubber composition as known from the septum part of any known drug container. The proximal part 52 and the distal part 53 is preferably self-sealing i.e they close by the inherent resiliency as the needle cannula 20 is removed from the penetration point.

Between injections as depicted in FIG. 6, when the spring 31 urges the shield 30 in the distal direction, the pointed tip 24 of the needle cannula 20 is moved to a position located inside the chamber 51 and is thus cleaned.

When the user performs an injection as disclosed in FIG. 7, the shield 30 is moved in the proximal direction (arrow "A") against the bias of the spring 31, and the pointed tip 24 of the needle cannula 20 penetrates through the distal part 53 of the cleaner 50. When doing so, the front part 23 of the needle cannula 20 is physically swept by the distal part 53.

When not in use, the distal end of the injection device 1 can be covered by a cap 4 as depicted in FIG. 8. In FIG. 8, the cap 4 is depicted in the process of being mounted as indicated by the arrow "B". As disclosed in FIG. 8, the cap 4 can distally be provided with a sponge 56 or the like treated with an anti-bacterial substance such that when the sponge 56 is pressed against the distal end or part 53 of the cleaner 50, the outer surface of its distal end 53 is cleaned.

Figure 11:
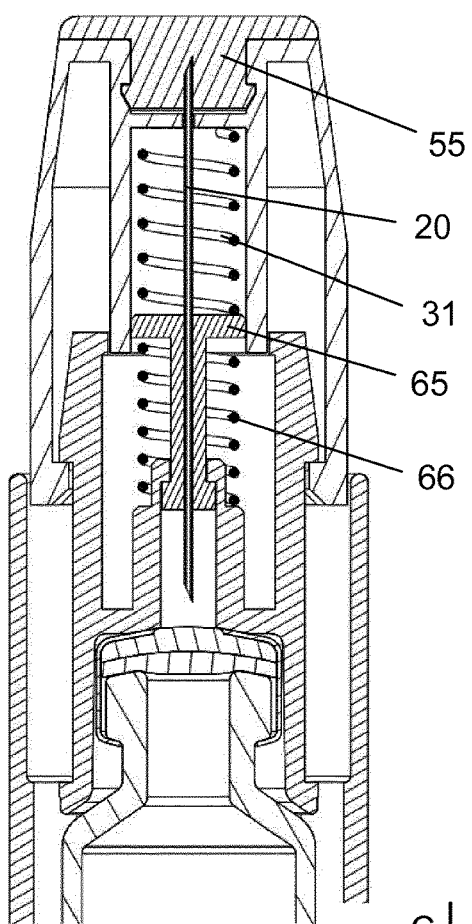
FIG. 11-13 show an embodiment having an axial movable needle cannula.
Figure 12:
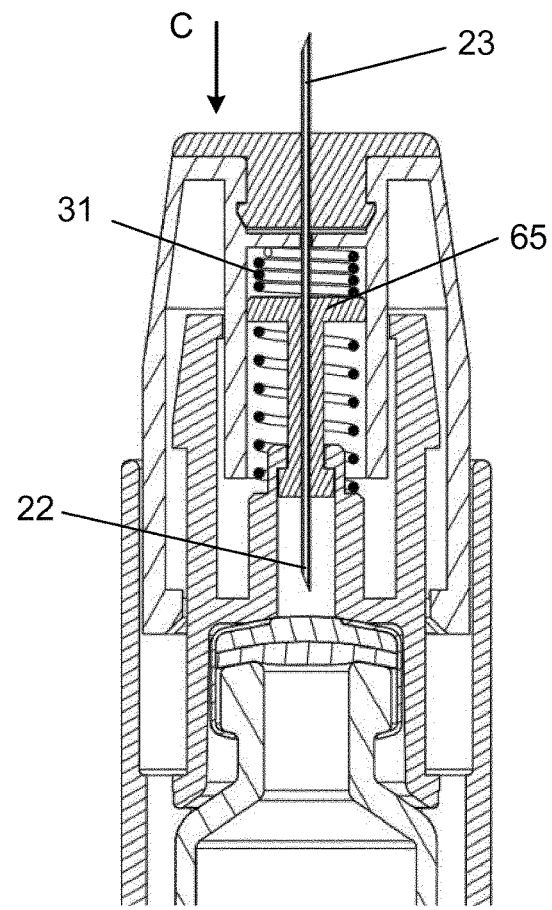
Figure 13:
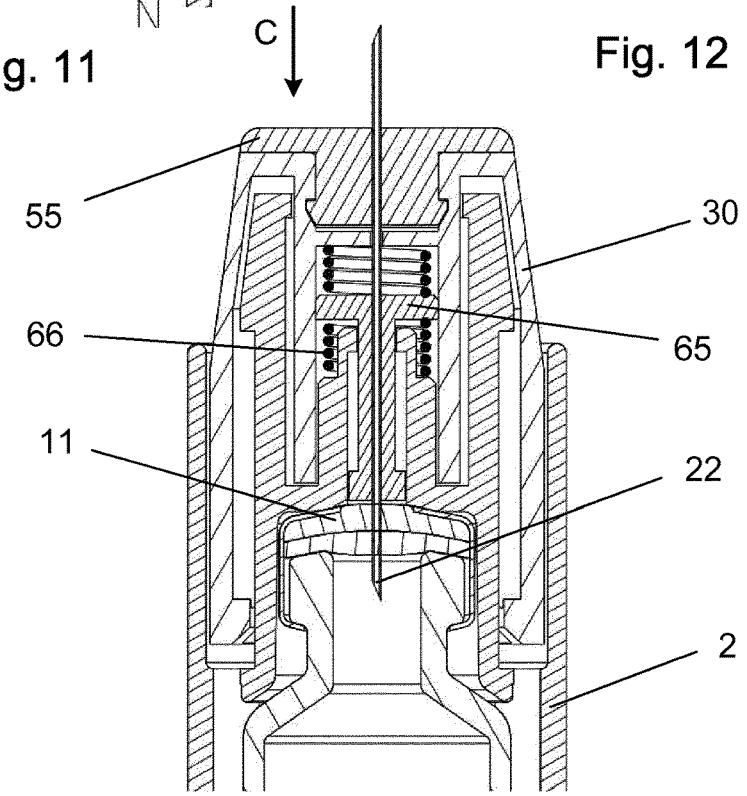

In an alternative embodiment, the chamber 51 can be solid such that the cleaner 50 is instead one solid plug 55 as depicted in the FIGS. 11 to 13. The cleaning is thus restricted to the physical engagement between the exterior of the needle cannula 20 and the material of the solid plug 55, which material can contain antibacterial particles.

FIG. 9 and FIG. 10 discloses an embodiment in which the proximal end 22 of the needle cannula 20 and the distal end 23 are connected by a flexible tube 25. Between injections a valve mechanism 60 comprising a plurality of squeeze arms 61 squeezes the flexible tube 25 such that flow passage through the needle cannula 20 is prevented.

During injection, a plurality of arms 32 provided proximally on the needle shield 30 releases the valve mechanism 60 such that the liquid drug can flow through the lumen 21 of the needle cannula 20 as depicted in FIG. 10.

FIGS. 11, 12 and 13 discloses an alternative way of prevented flow passage through the lumen 21 of the needle cannula 20. The needle cannula 20 is secured in a movable hub 65 which is able to move axially between an extended position (FIG. 11) and a retracted position (FIG. 13). A hub spring 66 is provided between the housing 2 and the movable hub 65 urging the movable hub 65 into its extended position. In this extended position, the proximal part 22 of the needle cannula 20 is located outside, and distally in front of, the septum 11 of the cartridge 10.

During injection, the user presses (arrow "C") the shield 30 against his or hers skin whereby the distal end 23 of the needle cannula 20 projects beyond the shield 30 as depicted in FIG. 12. This happens against the bias of the spring 31. A further pressure as depicted in FIG. 14 moves the movable hub 65 in the proximal direction against the bias of the hub spring 66 whereby the proximal end 22 of the needle cannula 20 penetrates through the septum 11 thereby creating liquid communication between the user and the interior of the drug cartridge 10 such that the liquid drug contained inside the cartridge 10 can flow into the user in accordance with the set dose.

The distribution of forces between the spring 31 and the hub spring 66 determines which of the shield 30 or the hub 65 that moves first once the pressure (arrow C) is applied.

Figure 14:
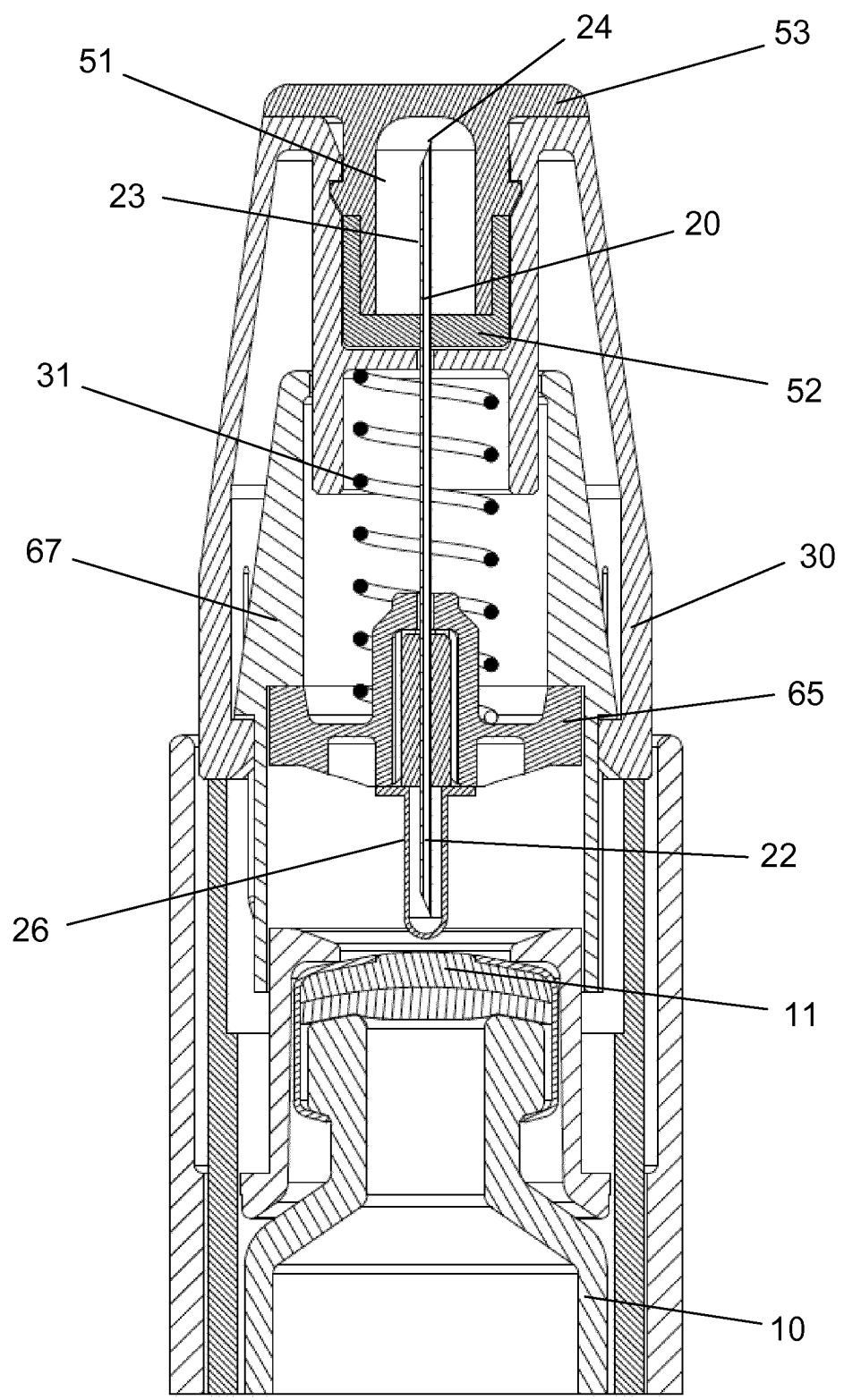
FIG. 14-16 show an embodiment having a connectable needle cannula.
Figure 15:
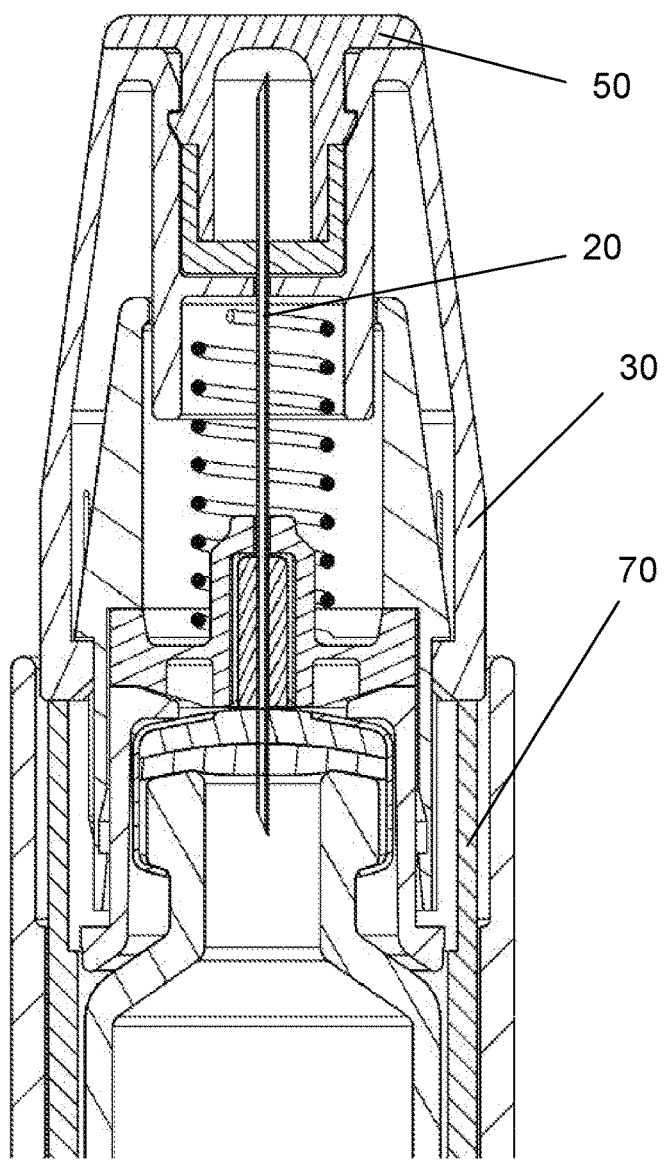
Figure 16:
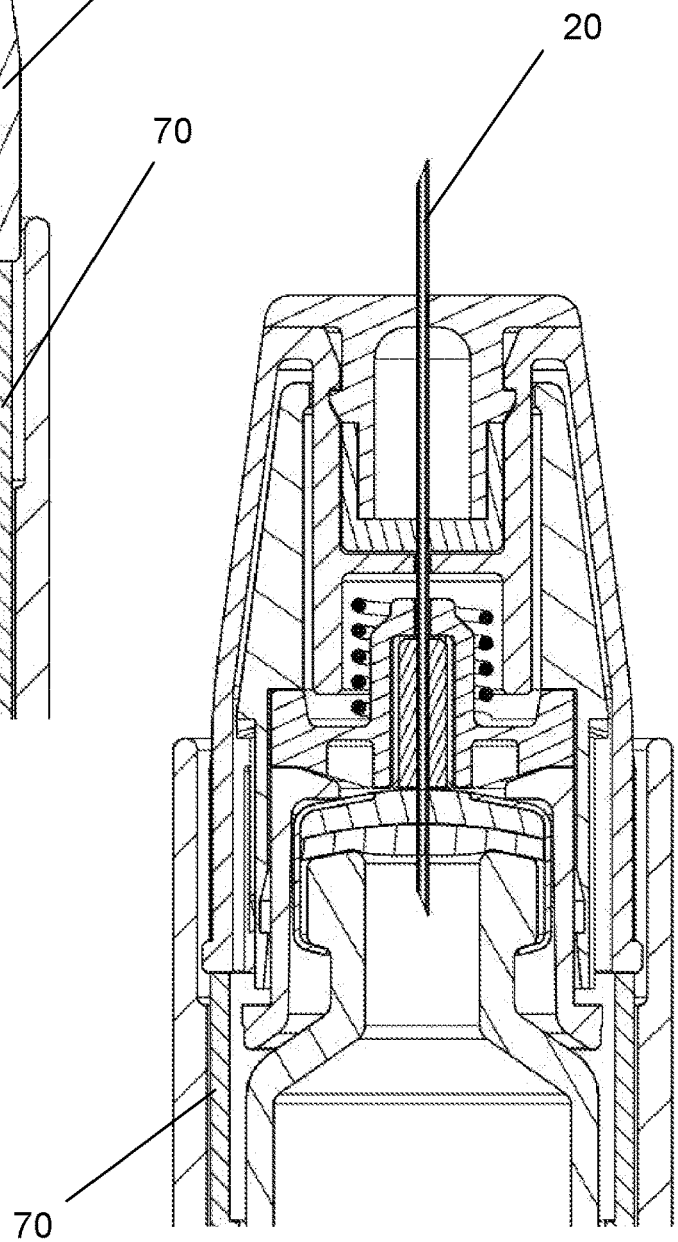

FIG. 14-16 discloses a similar embodiment. FIG. 14 depictures the shield 30 in its default position prior to injection, in which position the proximal end 22 is protected by a sterility barrier 26, which can e.g. be a latex bag sealed to the movable hub 65. When a user applies a pressure (arrow "D" in FIG. 15) by pushing the shield 30 against the skin an intermediate piece 67 which couples the shield 30 to the movable hub 65 is moved in the proximal direction. This proximal movement is transferred to the movable hub 65 and thus to the needle cannula 20. Ultimately, the proximal end 22 of the needle cannula 20 penetrates through its sterility barrier 26 and through the septum 11 as depicted in FIG. 15. In this position the intermediate part 67 and/or the movable hub 65 locks such that the proximal end 22 remains inserted through the septum 11 as depicted in FIG. 16. Once the pressure (arrow D) is removed (FIG. 16) the spring 31 urges the shield 30 back into its extended position whereas the intermediate piece 67 and the movable hub 65 remain in their locked position.

The intermediate piece 67 is preferably provided with stops 68 cooperating with similar stops 34 provided on the shield 30 to stop the shield 30 in its extended position.

Figure 17:
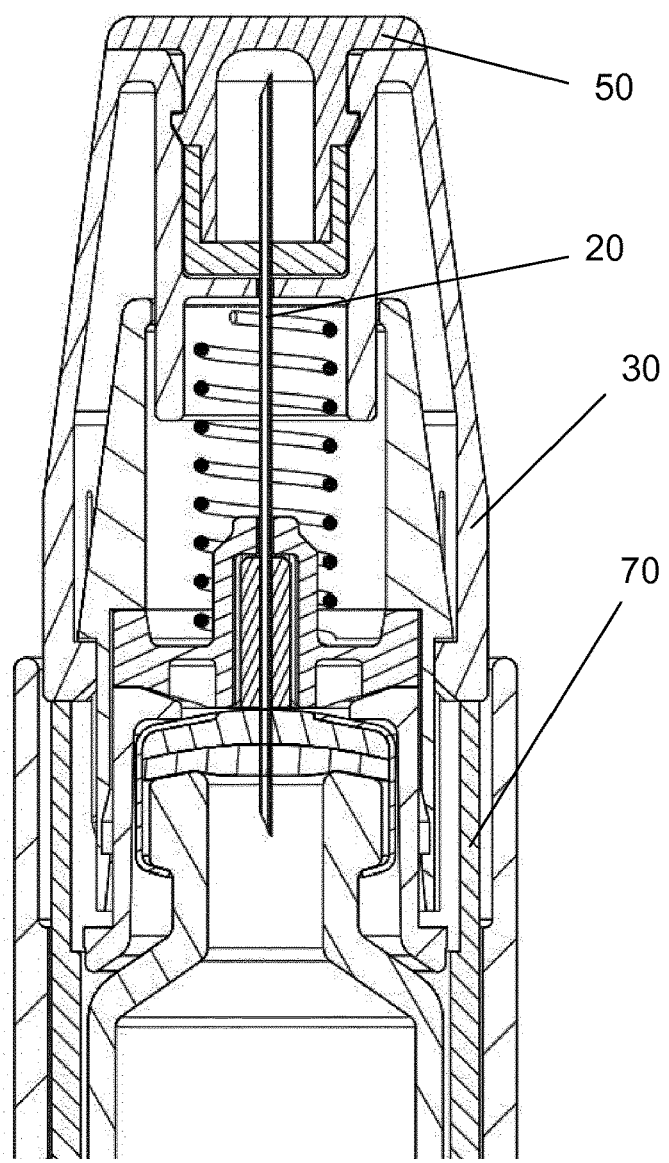
FIG. 17-18 show a locking mechanism for the needle shield.
Figure 18:
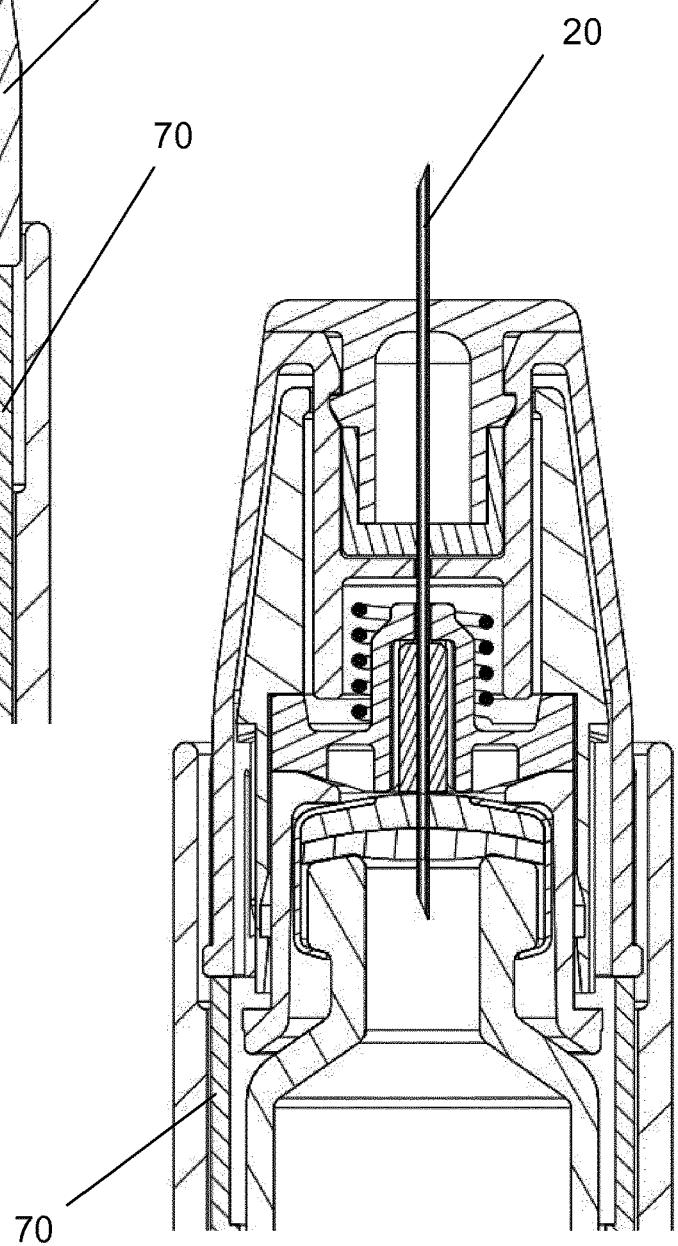

FIG. 17 and FIG. 18 discloses an embodiment in which the shield 30 is prevented from moving in the proximal direction by a locking shield 70. This locking shield 70 cooperates with the dose setting button 3 in the following manor.

When no dose has been set, the locking shield 70 prevents the proximal movement of the shield 30. When the user sets a dose i.e. the non-shown scale drum is rotated away from its zero position, the locking shield 70 moves either rotational or proximal to a position allowing the shield 30 to move proximally.

After injection, the scale drum automatically returns to its zero position where after the user removes the needle cannula 20 from the skin. When no force is applied to the distal end of the shield 30 it returns to its initial position covering the pointed tip 24 of the needle cannula 20 where after the locking shield 70 returns to its blocking position preventing the shield 30 from moving proximally until next time the user dials a new dose to be injected.

Figures 19, 20:
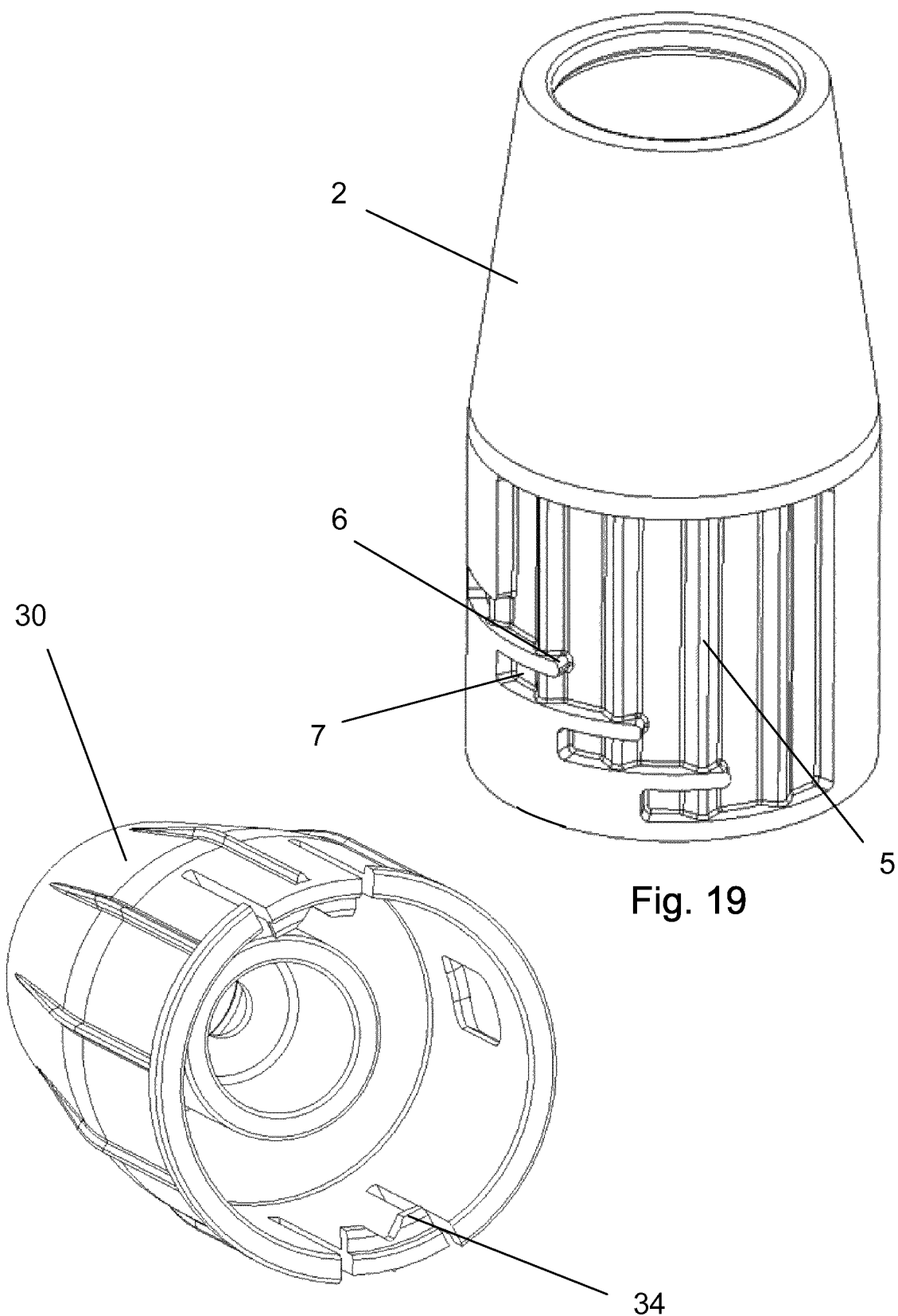
FIG. 19-20 show a mechanism for setting an individual injection depth.

FIG. 19 and FIG. 20 discloses the distal end of the housing 2 of an embodiment of the injection device 1. The distal part of the housing 2 is provided with a plurality of longitudinal ridges 5. These ridges 5 guides flexible arms 34 provided on the shield 30 as depicted in FIG. 20 such that the needle shield 30 can slide axially in relation to the housing 2.

Each ridge 5 has a specific axial length which is determined by the position of a plurality of axial stops 6. These stops 6 each prevents further axial movement of the needle shield 30. If the user rotates the needle shield 30 when in the stopping position, the needle shield 30 can be parked in its retracted position due to the gap 7 provided rotational aligned with each stop 6.

Prior to each injection, the user can rotate the shield 30 relatively to the housing 2 thereby determining the axial length the shield 30 can move which in turn is decisive for the depth into the subcutaneous layer of the user the distal part 23 of the needle cannula 20 penetrates during injection. The axial length available in each position could e.g. be printed on the shield 30.

Some preferred embodiments have been shown in the foregoing, but it should be stressed that the invention is not limited to these, but may be embodied in other ways within the subject matter defined in the following claims.

The invention claimed is:

1. A pre-filled disposable injection device having a needle cannula permanently mounted thereon, comprising:
   a housing containing a non-exchangeable cartridge for storing a liquid drug sufficient for a number of injections, and which cartridge is permanently embedded in the injection device,
   a settable dose setting mechanism having a dose setting button whereby a user can set a size of a dose to be injected,
   the needle cannula, which is maintained attached to the injection device between injections and permanently mounted to the housing of the injection device and follows a life cycle of the pre-filled injection device, comprising a front part having a tip for penetrating skin of the user, a back part for penetrating into the cartridge, and a lumen usable for passage of the liquid drug in the non-exchangeable cartridge through an initial injection followed by a successive number of injections sufficient to deplete the liquid drug in the cartridge,
   a telescopic needle covering shield distally carrying a cleaner comprising a hollow chamber containing a liquid cleaning solvent, and which shield can operate between a first position and a second position;
      the first position being a position in which the telescopic shield is in an extended position covering the tip of the front part of the needle cannula,
      the second position being a position in which the shield is retracted such that at least the tip of the front part of the needle cannula is exposed to perform an injection, and
   wherein at least the lumen of the needle cannula is preserved in a sterile condition prior to the initial injection and wherein a resilient structure automatically returns the shield to the first position following both the initial injection and any of the successive injections, and in which the first position at least the tip of the front part of the needle cannula is contained within the cleaner to thereby prevent clogging of the lumen of the needle cannula,
   wherein the shield allows for a plurality of doses where the shield operates between the first position and the second position a plurality of times.

2. A pre-filled disposable injection device according to claim 1, wherein the pre-filled injection device with the needle cannula mounted thereon is packed in a sterile container thereby maintaining sterility of the lumen of the needle cannula prior to the initial injection.

3. A pre-filled disposable injection device according to claim 1, wherein the lumen of the needle cannula is preserved sterile prior to the initial injection, the lumen is covered by a cover or a cap having a sterile interior.

4. A pre-filled disposable injection device according to claim 1, wherein the length of the front-part of the needle cannula extending beyond the needle shield in the second position is settable by a user.

* * * * *

UNITED STATES PATENT AND TRADEMARK OFFICE
CERTIFICATE OF CORRECTION

Page 1 of 1

PATENT NO. : 11,007,327 B2
APPLICATION NO. : 14/437389
DATED : May 18, 2021
INVENTOR(S) : Bengtsson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this
Sixth Day of December, 2022

Katherine Kelly Vidal
*Director of the United States Patent and Trademark Office*